United States Patent
Van Den Berg et al.

(10) Patent No.: US 11,098,011 B2
(45) Date of Patent: Aug. 24, 2021

(54) PROCESS FOR PREPARING A POWDERY ORGANIC PEROXIDE FORMULATION

(71) Applicant: NOURYON CHEMICALS INTERNATIONAL B.V., Arnhem (NL)

(72) Inventors: Michel Van Den Berg, Elst (NL); Johannes Willibrordus Antonius Overkamp, Lemelerveld (NL); Auke Gerardus Talma, Bathmen (NL); Edgard Everick Krosendijk, Deventer (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/954,551

(22) PCT Filed: Dec. 14, 2018

(86) PCT No.: PCT/EP2018/084885
§ 371 (c)(1),
(2) Date: Jun. 17, 2020

(87) PCT Pub. No.: WO2019/121366
PCT Pub. Date: Jun. 27, 2019

(65) Prior Publication Data
US 2020/0331854 A1  Oct. 22, 2020

(30) Foreign Application Priority Data

Dec. 19, 2017 (EP) .................................... 17208545

(51) Int. Cl.
*C07C 407/00* (2006.01)
*C08K 5/14* (2006.01)
(52) U.S. Cl.
CPC ............ *C07C 407/006* (2013.01); *C08K 5/14* (2013.01)
(58) Field of Classification Search
CPC .............................. C07C 407/006; C08K 5/14
USPC ........................................................ 568/599
See application file for complete search history.

(56) References Cited

U.S. PATENT DOCUMENTS 3,538,011 A  11/1970  Van Der Klaauw et al.

FOREIGN PATENT DOCUMENTS

EP   2709982 A1 *  3/2014  ......... C07C 407/006
EP   2709982 A1     3/2014

OTHER PUBLICATIONS

EPO, European Extended Search Report issued in European Application No. 17208545.8, dated Jun. 7, 2018.
ISA-EPO, International Search Report issued in International Application No. PCT/EP2018/084885, dated Mar. 8, 2019.
Nicoll, W.D., et al. "Stability of Dilute Alkaline Solutions of Hydrogen Peroxide", Industrial and Engineering Chemistry, Dec. 1955, pp. 2548-2554, vol. 47, No. 12.

* cited by examiner

*Primary Examiner* — Deborah D Carr
(74) *Attorney, Agent, or Firm* — Lorenz & Kopf, LLP

(57) ABSTRACT

Process for preparing a powdery organic peroxide formulation, said process comprises the following steps:
a) preparing a reaction mixture comprising:
40-80 wt % water
10-25 wt % of an acid chloride or chloroformate,
1-4 wt % hydrogen peroxide,
2-8 wt % alkali metal hydroxide,
1-25 wt % of a phlegmatizer selected from the group consisting of ethylene glycol dibenzoate, phenyl benzoate, trimethylol propane tribenzoate, glyceryl tribenzoate, ethylene glycol ditoluate, 1,3-propanediol ditoluate, ethylene glycol 4-tert-butylbenzoate, ethylene glycol monobenzoate monotoluate, 2,3-butanediol dibenzoate, 4-methylphenyl benzoate acid ester, trimethylolpropane dibenzoate, and combinations thereof
0.002-0.20 wt % of a surfactant, and
0.25-5.0 wt % of an inert organic solvent,
all percentages based on the weight of the reaction mixture,
b) heating the reaction mixture at a temperature in the range 5-50° C.

20 Claims, No Drawings

US 11,098,011 B2

PROCESS FOR PREPARING A POWDERY ORGANIC PEROXIDE FORMULATION

CROSS-REFERENCE TO RELATED APPLICATION

This application is a U.S. National-Stage entry under 35 U.S.C. § 371 based on International Application No. PCT/EP2018/084885, filed Dec. 14, 2018, which was published under PCT Article 21(2) and which claims priority to European Application No. 17208545.8, filed Dec. 19, 2017, which are all hereby incorporated in their entirety by reference.

TECHNICAL FIELD

The present invention relates to a process for the preparation of storage stable and safe powdery organic peroxide formulations.

BACKGROUND

As is well-known, organic peroxides are thermally labile organic compounds. Because the decomposition of peroxide is exothermic, it is hazardous when the heat of decomposition cannot be dissipated, e.g., by heat loss to the surrounding area. When heat build-up occurs, the decomposition reaction eventually becomes uncontrollable and potentially dangerous. To avoid such undesired situations, the peroxide is typically formulated with one or more phlegmatizing agents, such as inert organic materials.

This phlegmatization can be done with a liquid phlegmatizer—resulting in a solution, paste, emulsion, or suspension of the peroxide in said phlegmatizer—or with a solid phlegmatizer. If the organic peroxide itself is in solid form, dilution with a solid phlegmatizer will give a solid mixture (i.e. a physical blend) of organic peroxide and solid phlegmatizer.

It is of course important that the phlegmatized organic peroxide is stable for a sufficiently long period, meaning that both components remain homogeneously mixed and do not segregate to form separate phases.

Organic peroxides find application in polymerization processes and crosslinking and curing of resinous materials. For these applications, it is important for the phlegmatized organic peroxide formulation to be quickly homogenized with the monomers to be polymerized or the resinous material to be cured or crosslinked.

Powdery organic peroxide formulations are disclosed in U.S. Pat. No. 3,538,011. Apart from an organic peroxide that is solid at room temperature, the formulation comprises a phlegmatizer that is solid at room temperature and has a melting point above 40° C. and below the decomposition temperature of the organic peroxide.

One of the solid organic peroxides disclosed in this document is dibenzoyl peroxide. Examples of disclosed phlegmatizers are phenyl benzoate and ethylene glycol dibenzoate.

This document discloses three methods of preparing the formulations. According to the first method, existing organic peroxide powder and phlegmatizer are mixed. According to the second method, the organic peroxide is produced in the presence of the phlegmatizer. The third method involves simultaneous production of the organic peroxide and the phlegmatizer, in the same mixture.

The second method is said to be preferred because it leads to more homogeneous and finer powders that more quickly dissolve in polyester resins.

EP 2 709 982 discloses the preparation of powdery organic peroxide formulations comprising a solid organic peroxide and, as phlegmatizer, an alkylbenzoate with a melting or softening point above 45° C. Disclosed alkyl benzoates are glyceryl tribenzoate, neopentylglycol dibenzoate, pentaerythritol tetrabenzoate, and 1,4-cyclohexanemethanoldibenzoate.

The formulations can be prepared by (i) physically mixing the organic peroxide and the phlegmatizer or (ii) producing the organic peroxide in the presence of the phlegmatizer. The latter method involves dissolving the phlegmatizer in a precursor of the peroxide (e.g. a ketone or acid chloride), and reacting the resulting solution with a hydrogen peroxide/sodium hydroxide solution to form the organic peroxide.

In an example, a dibenzoyl peroxide/glyceryl tribenzoate formulation was prepared by adding a solution of glyceryl tribenzoate in benzoyl chloride to an aqueous solution of sodium hydroxide, hydrogen peroxide, and a surfactant (Na-alkylbenzoylsulfonate), followed by collecting, washing, and drying the formed granulate.

It has been observed that these prior art processes of preparing powdery organic peroxide formulations in a solid phlegmatizer suffer from a number of problems. First of all, the yield is rather limited and requires improvement. Second, the reaction mixture tends to foam, which makes separation of the final product difficult and inefficient. Third, the prior art processes lead either to rather coarse particles, that dissolve rather slowly in resin systems, which may lead to hot spots in cure, or to very fine particles that are difficult to isolate.

The object of the present invention is, therefore, the provision of a process that solves these problems. In addition, other objects, desirable features and characteristics will become apparent from the subsequent summary and detailed description, and the appended claims, taken in conjunction with the accompanying drawings and this background.

SUMMARY

The present invention relates to a process for preparing a powdery organic peroxide formulation, said process comprises the following steps:
a) preparing a reaction mixture comprising:
    40-80 wt % water
    10-25 wt % of an acid chloride or chloroformate,
    1-4 wt % hydrogen peroxide,
    2-8 wt % alkali metal hydroxide,
    1-25 wt % of a phlegmatizer selected from the group consisting of ethylene glycol dibenzoate, phenyl benzoate, trimethylol propane tribenzoate, glyceryl tribenzoate, ethylene glycol ditoluate, 1,3-propanediol ditoluate, ethylene glycol 4-tert-butylbenzoate, ethylene glycol monobenzoate monotoluate, 2,3-butanediol dibenzoate, 4-methylphenyl benzoate acid ester, trimethylolpropane dibenzoate, and combinations thereof
    0.002-0.20 wt % of a surfactant, and
    0.25-5.0 wt % of an inert organic solvent,
    all percentages based on the weight of the reaction mixture, and
b) heating the reaction mixture at a temperature in the range 5-50° C.

DESCRIPTION

The following detailed description is merely exemplary in nature and is not intended to limit the invention or the application and uses of the invention. Furthermore, there is no intention to be bound by any theory presented in the preceding background of the invention or the following detailed description.

Water is present in the reaction mixture in a concentration of 40-80 wt %, preferably 50-75 wt %, more preferably 50-65 wt %, and most preferably 50-55 wt %, based on the total weight of the reaction mixture.

Preferred acid chlorides are benzoyl chloride, p-methylbenzoyl chloride, m-methylbenzoyl chloride, methoxy-substituted benzoyl chloride, and 2,4-dichlorobenzoyl chloride, which will result in the respective formation of dibenzoyl peroxide, di(p-methylbenzoyl)peroxide, di(m-methylbenzoyl)peroxide, and di(2,4-dichlorobenzoyl) peroxide. Benzoyl chloride is the most preferred acid chloride.

Preferred chloroformates are 4-tertbutylcyclohexyl chloroformate, cetyl chloroformate, and myristyl chloroformate, which will result in the respective formation of di(4-tertbutylcyclohexyl)peroxydicarbonate, dicetyl peroxydicarbonate, and dimyristyl peroxydicarbonate.

The chloroformate or acid chloride is present in the reaction mixture in a concentration of 10-25 wt %, preferably 15-25 wt %, and most preferably 20-25 wt %, based on the total weight of the reaction mixture.

Hydrogen peroxide is present in the reaction mixture in a concentration of 1-4 wt %, based on the total weight of the reaction mixture.

Suitable alkali metal hydroxides include NaOH and KOH, with NaOH being the most preferred. The alkali metal hydroxide is present in the reaction mixture in a concentration of 2-8 wt %, based on the total weight of the reaction mixture.

The phlegmatizer should have a melting point above 50° C. and should be soluble in the acid chloride or chloroformate. In addition, it should be soluble in the unsaturated polyester, vinyl ester, or (meth)acrylate resin that will be cured with the powdery organic peroxide formulation. Phlegmatizers satisfying these criteria are ethylene glycol dibenzoate (EGDB), phenyl benzoate, trimethylol propane tribenzoate, glyceryl tribenzoate, ethylene glycol ditoluate, 1,3-propanediol ditoluate, ethylene glycol 4-tert-butylbenzoate, ethylene glycol monobenzoate monotoluate, 2,3-butanediol dibenzoate, 4-methylphenyl benzoate acid ester, and combinations thereof.

Preferred phlegmatizers are ethylene glycol dibenzoate (EGDB), phenyl benzoate, and/or trimethylolpropane tribenzoate, because these phlegmatizers and formulations containing these phlegmatizers dissolve more quickly in unsaturated polyester and acrylate resins. Furthermore, they can be prepared in aqueous medium and can also be prepared in situ in benzoyl chloride.

The phlegmatizer is present in the reaction mixture in a concentration of 1-25 wt %, preferably 8-20 wt %, and most preferably 15-20 wt %, based on the total weight of the reaction mixture.

Examples of suitable surfactants are anionic surfactants like alkyl and aryl sulfonates, such as sodium dodecylbenzenesulfonate (SDBS) sodium lauryl ether sulfate (SLES), sodium dodecylsulfate (SDS), sodium 2-methyl-7-ethyl-undecyl-4-sulfonate, ammonium secondary alcohol ethoxysulfate (Tergitol™ 15-S-3A) and sodium N-methyl-N-oleoyl taurate (Hostapon® TPHC). Also suitable are non-ionic surfactants like polyoxyethylene sorbitan monolaurate, sorbitan monolaurate, sorbitan tristearate, glyceryl monostearate, and cellulose ethers (Methocel™). Cationic surfactants like N-alkyl trimethyl ammonium chloride (Arquad® 12/50) can also be used.

The surfactant is present in the reaction mixture in a concentration of 0.002-0.20 wt %, preferably 0.005-0.10 wt %, more preferably 0.005-0.05 wt %, even more preferably 0.005-0.02 wt %, and most preferably 0.005-0.01 wt %, based on the total weight of the reaction mixture and calculated as active component. Higher concentrations lead to foaming, dusting, and difficult filtration of the resulting product due to the very small particles formed. Lower concentrations lead to lower solubility of the powdery formulation in resins, which then requires longer mixing times and/or the creation of hot spots during resin cure.

The inert organic solvent acts as a co-solvent and serves to improve the yield and conversion of the organic peroxide synthesis, thereby reducing the amount of residual acid chloride or chloroformate in the final product. The solvent should be inert in the sense that it does not react with chloroformates and acid chlorides.

Examples of suitable inert organic solvents are chlorinated solvents, including methylene chloride, chloroform, tetrachloromethane, and trichloromethane; alkanes, including heptane and petroleum ether; ethyl acetate; and ethers, including cyclopentyl methyl ether (CPME) and methyl tert-butyl ether (MTBE).

Preferred inert organic solvents are methylene chloride and ethers, including cyclopentyl methyl ether (CPME) and methyl tert-butyl ether (MTBE). These solvents have similar polarities.

Alkanes are less preferred since they are inflammable and may start burning during drying of the formulation. Because of their lower polarity, alkanes also require higher amounts to be used and lead to courser particles.

The inert organic solvent is present in the reaction mixture in a concentration of 0.25-2.5 wt %, preferably 0.5-2.0 wt %, and most preferably 0.5-1 wt %, based on the total weight of the reaction mixture.

The process preferably involves the use of a H2O2 stabilizer. This compound is therefore optional.

A H2O2 stabilizer is defined as a metal ion scavenger. Metal ion scavengers trap or neutralize metal species that catalyse the decomposition of H2O2, as explained in W. D. Nicoll, A. F. Smith, Industrial and Engineering Chemistry, 47, 2548-2554 (1955).

A preferred H2O2 stabilizer is MgSO4, since this stabilizer also acts as antifoaming agent. Foaming negatively affects the separation of the organic and aqueous phases after the reaction.

Other H2O2 stabilizers that can be used include CaSO4; amino-methylenephosphonic acids like hydroxyethylidene-1,1-diphosphonic acid, ethylenediamine-tetra(methylenephosphonic acid), hexamethylenediamine-tetra(methylenephosphonic acid), and diethylenetriamine-penta (methylenephosphonic acid); carboxylic acids like ethylenediamine-tetraacetic acid (EDTA), diethylenetriamine-pentaacetic acid, N,N-bis(carboxymethyl)glycine, sodium citrate, and sodium tartrate; ethylenediamine; dimethylglyoxime; sodium pyrophosphate; and sodium silicate.

If present, the H2O2 stabilizer is preferably present in the reaction mixture in a concentration of 0.002-0.6 wt %, more preferably 0.005-0.4 wt %, based on the total weight of the reaction mixture.

The desired type and amount of H2O2 stabilizer to be present depends on the degree of metal contamination in the reaction mixture, the pH, the reaction temperature, and the reaction time.

For instance, at pH>10.5, MgSO4 is the preferred stabilizer. It is preferably used in concentration of 0.002-0.05 wt %, more preferably 0.005-0.02 wt %, and most preferably 0.005-0.01 wt %, based on the total weight of the reaction mixture.

At pH<10.5, the other H2O2 stabilizers mentioned above are preferred. They are preferably used in concentrations of 0.1-0.6 wt %, more preferably 0.2-0.4 wt %, and most preferably 0.3-0.4 wt %, based on the total weight of the reaction mixture.

In the process according to the present invention, the ingredients can be added in any order. However, it is preferred to first (slowly) dose H2O2 and the other components to a mixture comprising at least part of the water and the optional H2O2 stabilizer.

Said other components are preferably added in liquid form. They can be added individually or as admixture. If not liquid at room temperature, the ingredient(s) or the admixture is/are preferably heated to enable the formation of a liquid phase.

Preferably, a heated, liquid mixture of the acid chloride or chloroformate, the phlegmatizer, and the inert organic solvent is dosed to the aqueous reaction mixture. In a more preferred embodiment, the remaining water and alkali metal hydroxide is dosed simultaneously with the acid chloride-containing mixture, in such a way that the pH of the reaction mixture remains in the range 10-14.

In a preferred embodiment, at least part of the H2O2 stabilizer is added to the mixture of phlegmatizer and acid chloride or chloroformate, in order to inactivate any traces of metals present in the phlegmatizer.

In a preferred embodiment, the phlegmatizer is added as a solution in the acid chloride or chloroformate.

In an even more preferred embodiment, the phlegmatizer is EGDB, the acid chloride is benzoyl chloride, and EGDB is added as a solution in benzoyl chloride.

Even more preferably, this solution is obtained by reacting benzoyl chloride and ethane-1,2-diol in a molar ratio 2.5:1-4.5:1, preferably 3.5:1-4.5:1, most preferably 4.0:1-4.5:1 at a temperature in the range 80-130° C., preferably 90-120° C., most preferably 100-120° C. During this reaction, formed HCl is removed from the reaction mixture, for instance by passing a nitrogen stream through the reaction mixture. Via this route, EGDB is prepared in an environmentally attractive way. Compared to the conventional Schotten-Baumann route—in which ethane-1,2-diol is reacted at about −5° C. with benzoyl chloride in a biphasic system comprising a base (e.g. NaOH) to bind the HCl—the above process does not create NaCl waste streams, gives EGDB in high yield, and does not lead to benzoyl chloride hydrolysis.

The reaction between hydrogen peroxide and acid chloride or chloroformate is conducted at a temperature in the range 5-50° C. The reaction with acid chloride is preferably conducted at 5-35° C., most preferably 10-30° C. The reaction with chloroformate is preferably conducted at 35-50° C., most preferably 40-45° C.

The reaction generally takes about 1-3 hours.

The resulting precipitate, which contains the organic peroxide and the phlegmatizer, is separated from the mixture, washed and dried. Separation can be performed by filtration, for instance using a Nutsch filter.

The powdery organic peroxide formulation preferably has a weight average particle size in the range 50-1000 microns, more preferably 100-500 microns; as determined with a sieve deck. Preferably, less than 10 wt %, more preferably less than 5 wt %, and most preferably less than 1 wt % of the particles has a size of more than 500 microns, as determined by sieve analysis. Preferably, less than 10 wt %, more preferably less than 5 wt %, and most preferably less than 2.5 wt % is smaller than 100 microns, in order to reduce dusting.

Particles that are too large can be sieved out and recycled to the reaction mixture.

The powdery organic peroxide formulation obtained by the process of the present invention finds use in polymer modification processes, cross-linking reactions, (mass) polymerization processes, and curing processes of, for example, unsaturated polyester resins, vinyl ester resins, and acrylate resins, including ortho-resins, iso-resins, iso-npg resins, and dicyclopentadiene (DCPD) resins. Examples of such resins are maleic, fumaric, allylic, vinylic, and epoxy-type materials.

Curing processes using the formulation of the present invention can be carried out at any temperature from −15° C. up to 250° C. Preferably, it is carried out at ambient temperatures commonly used in applications such as hand lay-up, spray-up, filament winding, resin transfer moulding, coating (e.g. gelcoat and standard coatings), button production, centrifugal casting, corrugated sheets or flat panels, relining systems, kitchen sinks via pouring compounds, etc. However, it can also be used in SMC, BMC, pultrusion techniques, filament winding, cured-in-place pipe (CIPP), and the manufacturing artificial stone, for which temperatures up to 180° C., more preferably in the range 60-140° C. are used.

Such cured compositions find use in various applications, including marine applications, road paints, chemical anchoring, roofing, construction, relining, pipes and tanks, flooring, windmill blades, laminates, etc.

EXAMPLES

Example 1

The reactor was successively charged with 248 g deionized water, 2.0 g of a 3.4 wt % $MgSO_4$ solution, and 1.89 g of a 5.6 wt % Hostapon® TPHC solution (containing 60 wt % active material). Next, 94.0 g of a 25% NaOH solution was added, followed by 31.5 g 70% $H_2O_2$.

Under intensive stirring (power input: 3.0 kw/m$^3$), a mixture of 171.3 g benzoyl chloride, 140.4 g ethyleneglycol dibenzoate, and 6.0 g dichloromethane, heated to a temperature ≥35° C., was dosed to the reactor within 60 minutes, keeping the pH at 12.4 by simultaneous dosing of 25% NaOH.

After a post reaction of 20 minutes at 30° C., the reaction mixture was filtered over a G-3 glass filter and washed with deionized water. The solids were dried in air, yielding 276 g of a powdery formulation of dibenzoyl peroxide in EGDB with a peroxide assay of 49.2%. The yield was 92.2%.

The particle size distribution of this powdery formulation was assessed with sieve analysis.

The results are displayed in Table 1.

In order to study the solubility of the formulation in different resins, 0.5 grams of the formulation was added to a 100 ml beaker containing 50 gram resin and stirred with an overhead pitched blade stirrer (40 mm) at 4 rpm. Dissolution speed was judged visually. The following resins were used:

Palatal® P4 (a styrene-containing unsaturated polyester resin ex-DSM)

Duracon® 205 (an acrylate resin ex-Polyplastics)

The formulation prepared in this Example dissolved in Palatal® P4 within 4-5 minutes and in Duracon® 205 within 3-4 minutes.

Comparative Example A

Example 1 was repeated, except that no surfactant (Hostapon® TPHC solution) was added to the reaction mixture.
As shown in Table 1, this resulted in courser particles. For this formulation, it required about 10 minutes to dissolve in Palatal® P4.

Example 2

Example 1 was repeated, except that 75 g of a 0.2 wt % Methocel® K99 solution was used instead of 1.89 g of a 5.6 wt % Hostapon® TPHC solution (containing 60 wt % active material).
The resulting particle size distribution is displayed in Table 1.

Example 3

Example 1 was repeated, except that 0.33 g LAS (15 wt % sodium dodecyl benzene sulfonate in water; Hoesch A E 15) was used instead of the 5.6 wt % Hostapon® TPHC solution.
The resulting particle size distribution is displayed in Table 1.

TABLE 1

| Example | <100 microns (wt %) | >500 microns (wt %) |
|---|---|---|
| 1 | 0.4 | 2.7 |
| 2 | 2.3 | 6.2 |
| 3 | 0.6 | 0.7 |
| A | 0.2 | 23.2 |

Comparative Example B

Example 1 was repeated, except that no dichloromethane was added to the reaction mixture. This process resulted in foaming of the reaction mixture and a yield of 89.0%.

Example 4

Example 1 was repeated, except that instead of a 3.4 wt % $MgSO_4$ solution, 2.86 g Dequest® 2066 (=a 25 wt % solution of diethylenetriamine penta(methylene-phosphonic) acid, sodium salt) was used and the pH was controlled as 10.5. Although this resulted in some foaming, the yield of the reaction was very high: 96%.

Example 5

Example 1 was repeated, except that the premix of benzoyl chloride, ethylene glycol dibenzoate, and dichloromethane was prepared as follows. Benzoyl chloride (320 g) was placed in a baffled reaction vessel. The reaction mixture was stirred with a turbine stirrer and heated to 115° C. Ethane-1,2-diol (33.5 g) was added dropwise over 270 minutes. The formed HCl was removed by a nitrogen flow through the reaction mixture. The relative molar ratio of ethylene glycol monobenzoate (EGMB) and EGDB after 30 minutes of post reaction was 0.04:0.96.
Methylene chloride was finally added to the resulting product, which was then used in the process of Example 1.

Example 6

The reactor was successively charged with 273 g deionized water, 300 g of a 0.2 wt % Methocel K99 solution, 1.5 g of a 3.4 wt % $MgSO_4$ solution, and 45.3 g 50% NaOH solution. Next, 15.4 g 70% $H_2O_2$ was added, while maintaining the temperature at 40° C. Under intensive stirring, a mixture of 125.2 g 4-t-butylcyclohexyl chloroformate, 15.5 g ethyleneglycol dibenzoate, and 8.5 g petroleum ether 60-80 was dosed within 1 minute at 40° C. After 60 minutes, the pH dropped to 10.0 and was then maintained at this value during 90 minutes, while dosing NaOH-50%. The mixture was neutralized with HCl-18% to pH 7 and filtered over a G-3 glass filter and washed with deionized water. The solids were dried in air yielding 126 g of a powdery formulation of di(4-tert-butylcyclohexyl)peroxydicarbonate in EGDB with a peroxide assay of 84.7%.

Example 7

The reactor was successively charged with 520 g deionized water, 0.9 g Tergitol AN-4 (sodium 2-methyl-7-ethyl-undecyl-4-sulfonate), 1.4 g of a 3.4 wt % MgSO4 solution and 41.0 g NaOH-50%. Next, 14.9 g H2O2-70% was added, while maintaining the temperature at 42° C. Under intensive stirring, a mixture of 113.5 g 4-t-butylcyclohexyl chloroformate, 38.6 g glyceryl tribenzoate, and 7.7 g petroleum ether 60-80, with a temperature ≥35° C., was dosed to the reaction mixture within 1 minute. After 70 minutes, the pH dropped to 10.0 and was was maintained at this value during 60 minutes by dosing NaOH-50%. The mixture was neutralized with HCl-18% to pH 7 and filtered over a G-3 glass filter and washed with deionized water. The solids were dried in air, yielding 135 g of di(4-tert-butylcyclohexyl)peroxydicarbonate in glyceryl tribenzoate with a peroxide assay of 72.2 wt %.

Comparative Example C

Example 1 of EP 2 709 982 was repeated, except that ethylene glycol dibenzoate (EGDB) was used instead of glyceryl tribenzoate (GTB), and the amounts were adjusted to 1 liter scale.
The reactor was successively charged with 1,345 g deionized water, 132 g 40 wt % NaOH, and 135 g ethyleneglycol dibenzoate (EGDB). The reactor was cooled at 5° C. Under intensive mixing, 10.3 g Na-dodecylbenzene sulfonate, 6 g isohexane, and 31 g 60% H2O2 were added.
At a temperature of 20° C., 71 g benzoylchloride was dosed in 10 minutes. After a post reaction of 20 minutes at 20° C., the reaction mixture was filtered under reduced pressure over a G3 glass filter. A lot of foam was formed and a lot of fines passed through the filter. Due to the very bad filtration, the solids on the filter were brought in a 1 L conical flask together with 300 g deionized water and mixed intensively. Then the solids were allowed to sink to the bottom. The hazy upper layer was removed and 500 g deionized water was added to and mixed intensively with the remaining solids in the conical flask. Again, the solids were allowed to sink to the bottom and the slightly hazy upper layer was removed. This procedure with adding 500 g deionized water was repeated 3 times.
The solids were finally filtered over the G-3 glass filter. The solids were dried in air, yielding a powdery formulation of dibenzoyl peroxide in EGDB with a peroxide assay of 48.3 wt %. The yield was 84.7%, calculated on benzoyl chloride.
The resulting product was a very fine powder.
The particle size distribution of the powder that was retained in the filter was assessed with sieve analysis. The results are displayed in Table 2.

Example 8

Example 1 was repeated except that glyceryl tribenzoate (GTB) was used instead of ethylene glycol dibenzoate (EGDB).

The yield was 89.5%; the amount of fines is displayed in Table 2.

Example 9

Example 1 was repeated except that isohexane was used instead of dichloromethane; in the same amount.

The yield was 93.2%; the amount of fines is displayed in Table 2.

Example 11

Example 1 was repeated with power input of 2.0 kw/m3, resulting in a yield of 93.2%, and only a very small number of fines.

Example 12

Example 1 was repeated with power input of 3.9 kw/m$^3$, resulting in a yield of 92.7%, and the same content of fines.

TABLE 2

| Example | <100 microns (wt %) |
|---|---|
| 1 | 0.4 |
| C | 26.7 |
| 8 | 0.9 |
| 9 | 0.5 |
| 11 | 0.2 |
| 12 | 0.9 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A process for preparing a powdery organic peroxide formulation, comprising:
   a) preparing a reaction mixture comprising:
   40-80 wt % water
   10-25 wt % of an acid chloride or chloroformate,
   1-4 wt % hydrogen peroxide,
   2-8 wt % alkali metal hydroxide,
   1-25 wt % of a phlegmatizer selected from the group consisting of ethylene glycol dibenzoate, phenyl benzoate, trimethylol propane tribenzoate, glyceryl tribenzoate, ethylene glycol ditoluate, 1,3-propanediol ditoluate, ethylene glycol 4-tert-butylbenzoate, ethylene glycol monobenzoate monotoluate, 2,3-butanediol dibenzoate, 4-methylphenyl benzoate acid ester, trimethylolpropane dibenzoate,
   0.002-0.20 wt % of a surfactant, and
   0.25-5.0 wt % of an inert organic solvent,
   wherein all percentages based on the weight of the reaction mixture, and
   b) heating the reaction mixture at a temperature in the range 5-50° C.,
   wherein less than 10 wt % of the powdery organic peroxide formulation has a particle size that is smaller than 100 microns.

2. The process according to claim 1, wherein the reaction mixture comprises an acid chloride selected from the group consisting of benzoyl chloride, p-methylbenzoyl chloride, m-methylbenzoyl chloride, methoxy-substituted benzoyl chloride, and 2,4-dichlorobenzoyl chloride.

3. The process according to claim 1, wherein the reaction mixture comprises a chloroformate selected from the group consisting of 4-tertbutylcyclohexyl chloroformate, cetyl chloroformate, and myristyl chloroformate.

4. The process according to claim 1, wherein the inert organic solvent is selected from the group consisting of chlorinated solvents, alkanes, ethyl acetate, and ethers.

5. The process according to claim 1, wherein the inert organic solvent comprises a solvent selected from the group consisting of methylene chloride, chloroform, tetrachloromethane, trichloromethane, heptane, petroleum ether, ethyl acetate, cyclopentyl methyl ether (CPME), and methyl tert-butyl ether (MTBE).

6. The process according to claim 1, wherein the surfactant comprises a linear alkyl(benzene)sulfonate.

7. The process according to claim 1, wherein the surfactant comprises sodium dodecylbenzenesulfonate (SDBS), sodium lauryl ether sulfate (SLES), sodium dodecylsulfate (SDS), or sodium N-methyl-N-oleoyl taurate.

8. The process according to claim 1, wherein the reaction mixture comprises a phlegmatizer selected from the group consisting of ethylene glycol dibenzoate (EGDB), phenyl benzoate, and trimethylolpropane tribenzoate.

9. The process according to claim 8, wherein the reaction mixture comprises ethylene glycol dibenzoate (EGDB).

10. The process according to claim 1, wherein the reaction mixture is prepared by combining a mixture comprising water, hydrogen peroxide, alkali metal hydroxide, surfactants, inert organic solvent, and $H_2O_2$ stabilizer, with a solution of the phlegmatizer in the acid chloride.

11. The process according to claim 1, wherein the reaction mixture is prepared by combining a mixture comprising water, hydrogen peroxide, alkali metal hydroxide, surfactant, inert organic solvent, and $H_2O_2$ stabilizer, with a solution of the phlegmatizer in the chloroformate.

12. The process according to claim 10, wherein the $H_2O_2$ stabilizer comprises $MgSO_4$ and wherein the acid chloride comprises benzoyl chloride, p-methylbenzoyl chloride, m-methylbenzoyl chloride, methoxy-substituted benzoyl chloride, or 2,4-dichlorobenzoyl chloride.

13. The process according to claim 12, wherein the acid chloride comprises benzoyl chloride and the phlegmatizer comprises ethylene glycol dibutyrate.

14. The process according to claim 13, wherein the solution of ethylene glycol dibenzoate in benzoyl chloride is obtained by reacting benzoyl chloride and ethane-1,2-diol in a molar ratio range from 2.5:1 to 4.5:1 or in a molar ratio range from 4:1 to 4.5:1 at a temperature in the range 80-130° C.

15. A powdery organic peroxide formulation made by the process according to claim 1.

16. A polymer modification process comprising curing an unsaturated resin using the powdery organic peroxide formulation according to claim 15.

17. The polymer modification process according to claim 16, wherein the resin comprises an unsaturated polyester resin, a vinyl ester resin, an acrylate resin, or a dicylopentadiene resin.

18. The polymer modification process of claim 1,
wherein the acid chloride or chloroformate comprises benzoyl chloride;
wherein the alkali metal hydroxide comprises sodium hydroxide;
wherein the phlegmatizer comprises ethylene glycol dibenzoate, glyceryl tribenzoate, or combinations thereof;
wherein the inert organic solvent comprises dichloromethane, isohexane, or combinations thereof;
wherein the surfactant comprises sodium methyl oleoyl taurate, hydroxypropylmethylcellulose, sodium dodecyl benzene sulfonate, or combinations thereof;
wherein the reaction mixture further comprises magnesium sulfate, diethylenetriamine penta(methylenephosphonic) acid, or combinations thereof;
wherein the benzoyl chloride, ethylene glycol dibenzoate, and dichloromethane are optionally premixed and then combined with ethane-1,2-diol to form HCl which is then removed; and
wherein less than 2.5 wt % of the powdery organic peroxide formulation has a particle size that is smaller than 100 microns.

19. The polymer modification process of claim 1,
wherein the acid chloride or chloroformate comprises 4-t-butylcyclohexyl chloroformate;
wherein the alkali metal hydroxide comprises sodium hydroxide;
wherein the phlegmatizer comprises ethylene glycol dibenzoate;
wherein the inert organic solvent comprises petroleum ether;
wherein the surfactant comprises hydroxypropylmethylcellulose; and
wherein the reaction mixture further comprises magnesium sulfate.

20. The polymer modification process of claim 1,
wherein the acid chloride or chloroformate comprises 4-t-butylcyclohexyl chloroformate;
wherein the alkali metal hydroxide comprises sodium hydroxide;
wherein the phlegmatizer comprises glyceryl tribenzoate;
wherein the inert organic solvent comprises petroleum ether;
wherein the surfactant comprises sodium 2-methyl-7-ethyl-undecyl-4-sulfonate; and
wherein the reaction mixture further comprises magnesium sulfate.

* * * * *